United States Patent [19]

Noack

[11] Patent Number: 5,312,429
[45] Date of Patent: May 17, 1994

[54] SCALPEL HANDLE AND BLADE RELEASE ASSEMBLY

[75] Inventor: William L. Noack, Saugus, Calif.

[73] Assignee: Devon Industries, Inc., Chatsworth, Calif.

[21] Appl. No.: 920,004

[22] Filed: Jul. 27, 1992

[51] Int. Cl.⁵ .............................................. A61B 17/32
[52] U.S. Cl. ........................................ 606/167; 30/339
[58] Field of Search .................. 606/166, 167, 125; 30/156–158, 339, 161, 162, 164, 151

[56] References Cited

U.S. PATENT DOCUMENTS

| 1,625,778 | 4/1927 | Nickerson | 606/167 |
| 3,187,431 | 6/1965 | Mattes | 30/339 |
| 3,367,335 | 2/1968 | Ward et al. | 606/167 |
| 4,340,059 | 7/1982 | Marinoff | 606/166 |
| 5,060,387 | 10/1991 | Doucette | 606/167 |
| 5,201,748 | 4/1993 | Newman et al. | 606/167 |

Primary Examiner—Jerome L. Kruter
Attorney, Agent, or Firm—Poms, Smith, Lande & Rose

[57] ABSTRACT

An apparatus is disclosed whereby a detachable surgical blade is easily and effectively removed from blade handle adapted for use with detachable surgical blades. The apparatus is a two part assembly comprising a scalpel handle and a blade release slide element. The handle includes a blade mounting tang on the proximal end thereof and a grip on the distal end thereof. The handle has dimensions such that a portion of the rear edge of the scalpel blade protrudes latitudinally beyond the perimeter of that portion of the grip adjacent to the tang. The blade release slide element is slidably mountable on the handle and is of a length such that, when in assembled relation with the handle, the blade release slide element extends forwardly from an intermediate section of the grip to a section of the grip rearward of the tang. The blade release slide element has a blade engaging and release ramp which inclines from the proximal end of the handle to the distal end of the handle as the blade mounting portion of the tang extends upwardly. Removal of the blade is accomplished by a one handed digitally activated sliding movement of the blade release slide element towards the proximal end of the handle whereby the blade engaging and release ramp engages the protruding portion of the rear edge of the blade causing the rear portion of the blade to flex upwardly and slide forward off the tang.

4 Claims, 1 Drawing Sheet

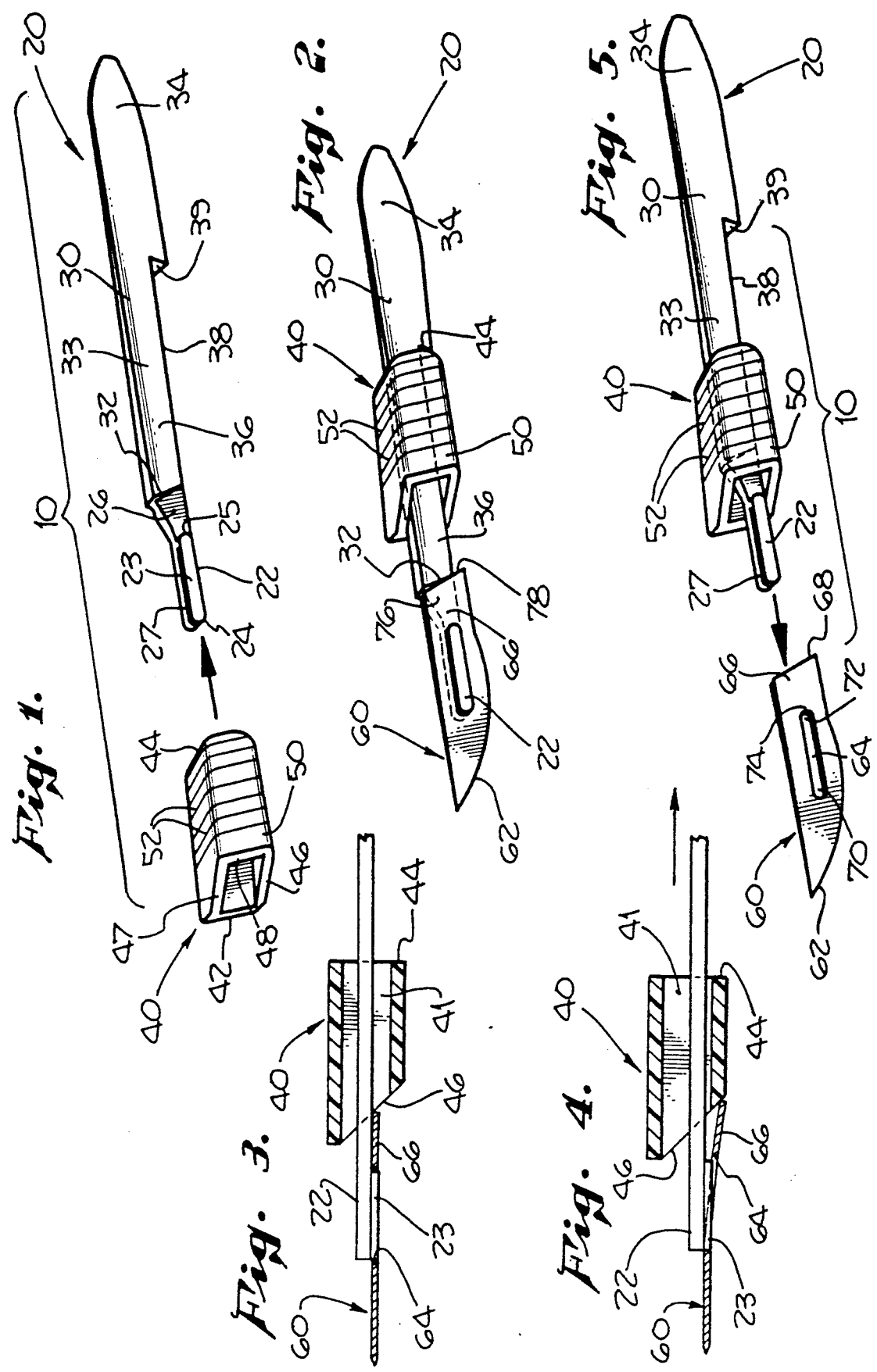

SCALPEL HANDLE AND BLADE RELEASE ASSEMBLY

BACKGROUND OF INVENTION

The present invention relates generally to apparatus for removing detachable surgical blades from a blade handle after use thereof in a surgical application. More particularly, the present invention relates to a handle mounted means for removing detachable scalpel blades from the proximal end of a scalpel handle after use thereof in a surgical application.

During the course of surgery, and thereafter, scalpel blades and the like must be replaced with new sterile blades. Due to the critical conditions under which scalpels are used, it is necessary to replace the blades fairly often and quickly. One type of scalpel commonly employed in surgical work comprises a handle having a tang with an upraised portion upon which a detachable blade is securely locked in place. The detachable blade for such a handle typically has a centrally located keyed slot with a narrow portion forward and a wide portion rearward. The tang has rounded forward and rear faces and opposed lateral grooves positioned in an intermediate latitudinal plane for slidably receiving the narrow portion of the keyed slot of the blade. With the aid of the grooves, the blade can be mounted on the handle by slidably positioning the inner rear edge of the keyed slot over the rounded rear face of the upraised portion of the tang. As the inner rear edge of the keyed slot is positioned over the rounded rear face of the upraised portion of the tang, the rearward portion of the blade snaps down into a recessed portion of the tang adjacent to the grip, locking the blade onto the handle.

Although assembly of a blade on the tang portion of a blade handle is rather an easy matter, the blade has heretofore been disengaged therefrom only with difficulty. Not only must a rearward portion of the blade be manually pried up over the top of the upraised portion of the tang, but in addition, an axial thrust must be applied to the flexed blade to effect complete disengagement of the blade from the handle. This simultaneous flexing and axial movement of a used blade to effect removal is not only awkward, but it can also be hazardous since the blade may carry viruses or other infectious diseases. As such, members of the surgical staff are reluctant to use forceps or hemostates to remove blades. If their hand slips, they may be accidentally cut and infected. Accordingly, it is the object of this invention to provide apparatus for disengaging a surgical blade from a blade handle in a ready and facile manner.

There have been prior attempts at constructing a device for removing blades safely as disclosed, by way of example, in prior U.S. Pat. No. 4,318,473. The device of that patent comprises a plurality of elements including a slot for slidably receiving the proximal end of a fully assembled scalpel and a shoulder positionable under the mounted blade for supporting the rear of the blade during blade disengagement procedures. To operate the device, the blade and handle must be slidably inserted into the slot and then manipulated downwardly. The downward movement of the assembled scalpel causes the rear portion of the blade to flex over the upraised portion of the tang. Thereafter, the handle must be withdrawn from the device. The device includes an element positioned to prevent rearward motion of the flexed blade as the handle is withdrawn from the device. Upon withdrawal of the handle from the device, the blade is disengaged from the handle.

While a used blade can be removed using devices such as disclosed in the above-referenced patent, such devices entail a plurality of elements and require a two handed manipulation of the scalpel handle and removal device to effect removal of the blade. It has therefore come to our attention that it would be desirable to provide an inexpensive handle mounted means for quickly and easily removing a used blade from a scalpel handle which can be manipulated by only one hand.

SUMMARY OF THE INVENTION

It is the primary object of the present invention to disclose and to provide an apparatus for removing a used detachable surgical blade from a blade handle in a single one handed motion. A further object of the present invention is to incorporate such an apparatus into a blade handle such that a blade can be quickly and easily removed from the handle without the use of a separate implement. A further object of the present invention is to provide and to disclose such an apparatus in a low cost assembly construction.

These objects are preferably accomplished using a two part assembly comprised of an improved scalpel handle and a blade release slide element which is slidably mountable thereon. The handle has a blade mounting tang at the proximal end thereof for holding a typical scalpel blade and a grip on the distal end thereof for holding the scalpel. The tang has an upraised portion at its forward end and a recessed portion at its rearward end. The upraised portion of the tang has opposed lateral grooves located in an intermediate latitudinal plane for slidably receiving a narrow portion of the keyed slot of a typical blade. The grip includes a forward section and a rearward section. The forward section has a reduced cross-sectional area having dimensions such that a portion of the rear edge of the chosen blade extends latitudinally beyond the perimeter of the portion of the grip adjacent to the recessed portion of the tang. The portion of the grip adjacent to the recessed portion of the tang has an abutment surface which is complementary contoured to and abuts the non-protruding portion of the rear edge of the blade.

The blade release slide element is shaped to define a substantially rectangular shaped bore having dimensions such that the blade release slide element is slidably mountable over the forward section of the grip. The blade release slide element has a leading end and a trailing end and is of a length such that, when in assembled relation with the handle, the blade release slide element extends forwardly from the juncture of the forward and rear sections of the grip to a section of the grip rearward of the tang. The leading end has a blade engaging and release ramp which inclines from the leading end to the trailing end as the tang extends upwardly from the recessed portion of the tang to the upraised portion of the tang. Removal of the blade is accomplished by a one handed digitally activated sliding movement of the blade release slide element towards the proximal end of the handle. More particularly, the initial movement of the blade release slide element towards the proximal end of the handle causes the blade engaging and release ramp to engage the protruding portion of the rear edge of the blade. Continued forward movement of the blade release and slide element causes the rearward portion of the blade to flex such that the rearward portion clears the upraised portion of the tang. Upon further forward movement of the blade release and slide element, the blade slides forwardly in the grooves of the tang until the narrow portion of the keyed slot of the blade disengages from the grooves whereupon the blade is disengaged from the handle.

Advantageously, the forward section of the grip is tapered to permit the blade release slide element to slidably engage the forward section of the grip in a fit sufficiently snug to ensure that the blade release slide element remains in a fixed position on the grip during the course of use of the blade without being so snug as to impair digitally activated sliding movement of the blade release slide element to effect disengagement of the blade after use. The grip also has a stop surface at the juncture of the forward section and the rearward section of the grip which abuts the trailing end of the blade release slide element in assembled relation to the handle thereby fixing the extent of rearward longitudinal movement of the blade release slide element during assembly thereof onto the handle.

It is submitted that those skilled in the art will obtain a better understanding of the construction and mode of operation of the present invention as well as become aware of additional advantageous and objects thereof from a consideration of the following detailed description of the preferred exemplary embodiment of the present invention taken in combination with the accompanying drawings as follows:

BRIEF DESCRIPTION OF THE DRAWINGS

FIG. 1 is a perspective view of the preferred exemplary embodiment of the present invention showing the scalpel handle and the blade release slide element in relational position prior to telescopic engagement.

FIG. 2 is a perspective view of the preferred exemplary embodiment of the present invention with a scalpel blade mounted thereon showing the scalpel handle and the blade release slide element in relational position after telescopic engagement.

FIG. 3 is a top section of a portion of the preferred exemplary embodiment of the present invention showing the position of the blade release slide element on the scalpel handle just prior to slidable engagement with the protruding portion of the rear edge of the mounted scalpel blade.

FIG. 4 is a top section of a portion of the preferred exemplary embodiment of the present invention showing the flexion of the rear portion of the blade subsequent to slidable engagement of the blade release slide element with the protruding rear edge of the blade.

FIG. 5 is a perspective view of the preferred exemplary embodiment of the present invention showing the scalpel handle and the blade release slide element in relational position upon complete disengagement of the scalpel blade from the scalpel handle.

DETAILED DESCRIPTION OF AN EXEMPLARY EMBODIMENT

Referring initially to FIGS. 1 and 5, the preferred exemplary embodiment of the present invention is shown generally at 10. As best shown in FIG. 1, the preferred exemplary embodiment is provided as a two part assembly having a scalpel handle 20 and the blade release slide element 40. Scalpel handle 20 has a blade mounting tang 22 at the proximal end for engaging a detachable scalpel blade and grip 30 on the distal end for holding the scalpel.

A typical detachable scalpel blade is shown generally as 60 in FIGS. 2 and 5. Scalpel blade 60 has a cutting edge 62, a centrally located keyed slot 64, a rear portion 66 and an angled rear edge 68. Keyed slot 64 has a narrow portion 70 at the forward end thereof and a wide portion 72 at the rearward end thereof. Blade 60 is typically made of a spring steel which provides blade 60 with some resiliency. It will be understood by those skilled in the art that blade 60, as described, does not form a part of the present invention. It will be further understood by those skilled in the art that the detachable blades contemplated for use with the present invention are conventional surgical implements which vary in size and shape depending upon the surgical application and include without limitation needles, saw blades and the like.

As best shown in FIG. 1, blade mounting tang 22 has an upraised portion 23 at the forward end of tang 22 and a recessed portion 26 at the rearward end of tang 22. Upraised portion 23 has a rounded forward face 24 and a rounded rearward face 25 and includes opposed lateral grooves 27 located in an intermediate latitudinal plane for slidably receiving narrow portion 70 of keyed slot 64. Upraised portion 23 is contoured for complemental engagement with keyed slot 64. With the aid of grooves 27, blade 60 can be mounted on handle 20 by inserting the forward end of tang into wide portion 72 of keyed slot 64 and slidably positioning rear inner edge 74 of keyed slot 64 over rounded rear face 25 of upraised portion 23. During this sliding process, rearward portion 66 of blade 60 is somewhat distorted from its planar configuration such that rearward portion 66 of blade 60 clears upraised portion 23. As rear inner edge 74 becomes positioned over rounded rear face 25, upraised portion 23 of tang 22 begins to fit within keyed slot 64 and rearward portion 66 of blade 60 snaps down into recessed portion 26 of tang 22. Blade 60 is thereby locked onto handle 20. When blade 60 is in assembled relation to handle 20, rear face 25 of upraised portion 23 engages rear inner edge 74 of keyed slot 64, thereby preventing blade 60 from slidably moving in grooves 27. Those skilled in the art will appreciate that the dimensions of tang 22 will vary with the size and shape of the keyed slot of the chosen blade in use.

In the preferred exemplary embodiment of the present invention as shown in FIGS. 1 and 2, the portion of grip 30 adjacent to recessed portion 26 includes an abutment surface 32 which is complementary contoured to and abuts non-protruding portion 76 of angled rear edge 68 when blade 60 is in assembled relation to handle 20. This helps to prevent movement of blade 60 during use in surgical applications.

As best shown in FIG. 1, grip 30 includes a forward section 33 and a rearward section 34. Forward section 33 has a reduced cross-sectional area 36 having dimensions such that protruding portion 78 of angled rear edge 68 extends latitudinally beyond the perimeter of the portion of grip 30 adjacent to recessed portion 26.

Grip 30 is shaped to accommodate the hand of the surgeon or other member of the surgical staff using the implement. Preferably, rearward section 34 is scored to enhance the gripping characteristics thereof. Other forms of scoring or roughening grip 30 may be employed within the scope of the present invention to provide an improved grip of handle 20.

In the preferred exemplary embodiment of the present invention as shown in FIGS. 3, 4, and 5, blade release slide element 40 is shaped to define a substantially rectangular shaped bore 41 having dimensions such that blade release slide element 40 is slidably mountable over forward section 33 of grip 30. Blade release slide element 40 includes leading end 42, trailing end 44, and two sets of opposing inner walls 47 and 48. Blade release slide element 40 is of a length such that, when in assembled relation with handle 20, blade release slide element 40 extends forwardly from the juncture of forward section 33 and rearward section 34 to a section of the grip slightly rearward of recessed portion 26. Leading end 42 includes a blade engaging and release ramp 46 which inclines from leading end 42 to trailing end 44 as upraised portion 23 of tang 22 extends upwardly from recessed portion 26. Removal of blade 60 is accomplished by a one handed digitally activated sliding movement of blade release slide element 40 towards the forward end of handle 20. As best shown in FIG. 3, forward movement of blade release slide element 40 towards the forward end of handle 20 causes blade engaging and release ramp 46 to engage protruding portion 78 of angled rear edge 68. Continued forward movement of blade release slide element 40 causes rearward portion 66 of blade 60 to flex such that rearward portion 66 clears upraised portion 23. Upon further forward movement of blade release slide element 40, blade 60 slides forwardly in grooves 27 until narrow portion 70 of keyed slot 64 is disengaged from grooves 26 whereupon blade 60 is disengaged from handle 20.

In the preferred exemplary embodiment of the present invention as best shown in FIG. 1, forward section 33 of grip 30 includes tapered surface 38 which is angled so that blade release slide element 40 slidably engages forward section 33 in a fit sufficiently snug to ensure that blade release slide element 40 remains in a fixed position on grip 30 during the course of use of blade 60 without being so snug as to impair digitally activated sliding movement of blade release slide element 40 to effect disengagement of blade 60 after use. Grip 30 also include stop surface 39 at the juncture of forward section 33 and rearward section 34 of grip 30. Stop surface 39 abuts trailing end 44 of blade release slide element 40 when blade release slide element 40 is in assembled relation to handle 20 thereby fixing the extent of rearward longitudinal movement of blade release slide element 40 during assembly thereof with handle 20. It will be understood by those skilled in the art that other methods may be employed to fix the position of blade slide element 40 on handle 20 and to ensure blade release slide element 40 remains in the desired position prior to initiating the procedure for blade disengagement.

Referring to FIG. 2, blade release slide element 40 also includes an outer surface 50 having a plurality of channels 52. The purpose of channels 52 is to facilitate grasping of handle 20 during surgery and to ensure that the digit or digits applied to blade release slide element 40 to effect blade disengagement do not slip on the surface of blade release slide element 40. However, it is to be understood by a person skilled in the art that any means of ensuring sufficient tactility of handle 20 and blade release slide element 40 may be employed including the use of non-planar configurations and composite materials with inherent tactile qualities.

The present invention contemplates that handle 20 and blade release slide element 40 are reusable and are composed of materials which can sustain sterilization by heating without damage. Handle 20 is typically made of material in the group of metals including stainless steel. Blade release slide element 40 is preferably composed of a plastic material which can be formed by injection molding and which is sufficiently pliant to permit repeated engagement and disengagement to and from handle 20.

It is seen therefore that a novel apparatus has been provided which readily enables a surgical blade to be disengaged from a blade handle in a single motion without the use of separate implement and without requiring any operator dexterity. The operator need only slidably urge the handle mounted blade release slide element in the forward direction to effect blade disengagement.

Although the present invention has thus been described in detail with regard to the preferred embodiment and drawings thereof, it should be apparent to those skilled in the art that various adaptations and modifications of the present invention may be accomplished which still fall with in the scope and spirit of the present invention. In particular, it will be appreciated by those skilled in the art that while the present invention contemplates the use of a two part assembly comprised of a blade handle and a blade release means which is slidably mountable thereon to effect blade disengagement, other configurations may be employed which do not entail the use of a two part assembly or which do not provide for slidable mounting of the blade release means on the blade handle. Similarly, while the present invention contemplates the use of a blade handle configured to expose a portion of the rear edge of the chosen blade in conjunction with a blade release slide element as described hereinabove to effect blade disengagement, those skilled in the art will appreciate that alternative handle mounted means may be employed to effect disengagement of a blade from other types of handles having a blade mounting tangs thereon. Accordingly, the scope of the present invention is not limited to the specific embodiment as illustrated herein, but is limited only by the following claims:

I claim:
1. A blade handle and release assembly adapted for use with a detachable surgical blade wherein said blade has a keyed slot with a wide portion and a narrow portion and wherein said blade has a rearward portion with a rear edge, said assembly comprising:
 a blade handle having a proximal end and a distal end with a blade mounting tang on said proximal end and a grip on said distal end; and
 a blade release slide element mounted on said grip for slidably engaging said blade and discharging said blade from said blade mounting tang via a one handed manipulation thereof;
 said blade mounting tang having an upraised portion contoured for complemental engagement with said keyed slot and a recessed portion adjacent to said grip for receiving said rearward portion of said blade;
 said grip having a forward section adjacent to said blade mounting tang with a reduced cross-sectional area having dimensions such that a portion of said rear edge of said blade protrudes latitudinally beyond the perimeter of said forward section and having a stop for holding said blade release means in a fixed position on said blade handle prior to initiation of the blade disengagement procedure;
 said forward section having an abutment surface adjacent to said recessed portion of said blade mounting tang which is complimentary contoured to abut a non-protruding portion of said rear edge of said blade;

said blade release slide element having a configuration such that said blade release slide element is slidably mountable over said forward section of said grip and having a blade engaging and release ramp for engaging said protruding portion of said rear edge and discharging said blade from said handle in response to a digitally activated sliding movement of said blade release slide element toward said proximal end of said blade handle, said blade engaging and release ramp inclining from said proximal end of said handle to said distal end of said handle as said blade mounting tang extends upwardly from said recessed portion of said blade mounting tang to said upraised portion of said blade mounting tang.

2. The assembly of claim 1 wherein said stop further comprises:

a tapered surface on said forward section of said grip such that said blade release slide element slidably engages said forward section in a fit sufficiently snug to ensure that said blade release slide element remains in a fixed position on said grip when said assembly is in use without being so snug as to impair digitally activated slidable movement of said blade release slide element for purposes of blade disengagement after said use.

3. The assembly of claim 2 wherein said grip further comprises:

a stop surface against which a trailing portion of said blade release slide element abuts when said blade release slide element is in assembled relation with said blade handle.

4. The assembly of claim 3 wherein said blade release slide element further comprises:

tactility means for improving the gripping characteristics of said blade release slide element.

* * * * *